(12) United States Patent
Roed et al.

(10) Patent No.: US 8,916,131 B2
(45) Date of Patent: Dec. 23, 2014

(54) RADIOPHARMACEUTICAL COMPOSITION

(75) Inventors: Line Roed, Oslo (NO); Sarah Elizabeth Peterson, Amersham (GB)

(73) Assignee: GE Healthcare Limited, Buckinghamshire (GB)

(*) Notice: Subject to any disclaimer, the term of this patent is extended or adjusted under 35 U.S.C. 154(b) by 383 days.

(21) Appl. No.: 12/673,602

(22) PCT Filed: Aug. 28, 2008

(86) PCT No.: PCT/EP2008/061275
§ 371 (c)(1),
(2), (4) Date: Feb. 16, 2010

(87) PCT Pub. No.: WO2009/027452
PCT Pub. Date: Mar. 5, 2009

(65) Prior Publication Data
US 2011/0008254 A1    Jan. 13, 2011

Related U.S. Application Data

(60) Provisional application No. 60/968,904, filed on Aug. 30, 2007.

(51) Int. Cl.
A61K 51/00 (2006.01)
A61M 36/14 (2006.01)
A61K 51/04 (2006.01)
A61K 47/10 (2006.01)
A61K 9/00 (2006.01)
A61K 47/26 (2006.01)

(52) U.S. Cl.
CPC .......... A61K 9/0019 (2013.01); A61K 51/0453 (2013.01); A61K 47/10 (2013.01); A61K 47/26 (2013.01)
USPC ........ 424/1.11; 424/1.89; 424/1.85; 424/1.81

(58) Field of Classification Search
None
See application file for complete search history.

(56) References Cited

U.S. PATENT DOCUMENTS

| | | | |
|---|---|---|---|
| 6,858,633 B1 * | 2/2005 | Stevens et al. | 514/367 |
| 2005/0043523 A1 * | 2/2005 | Klunk et al. | 534/11 |
| 2005/0123477 A1 * | 6/2005 | Wilson et al. | 424/9.6 |

FOREIGN PATENT DOCUMENTS

| | | |
|---|---|---|
| EP | 0017355 | 10/1980 |
| WO | 02/16333 | 2/2002 |
| WO | 2004/083195 | 9/2004 |
| WO | 2006/014381 | 2/2006 |
| WO | 2007/002540 | 1/2007 |
| WO | WO 2007020400 A1 * | 2/2007 |
| WO | 2007/064773 | 6/2007 |
| WO | 2008/134618 | 11/2008 |

OTHER PUBLICATIONS

Ametamet et al. J Nucl. Med. Biol. 2006; 47: 698-705.*
Klok et al. Nucl. Med. Biol 33 (2006) 935-938.*
Powell et al. PDA J. Pharm. Sci. Tech. 1998, 52, 238-311.*
Zhuang, Z-P, et.al. "Ibox(2-(4'-Dimethylaminophenyl)-6-Iodoben Zaxazole): A Ligand for Imaging Amyloid Plaques in the Brain" Nuclear Medicine and Biology, Elsevier, NY, US., vol. 28, No. 8, Nov. 1, 2001, pp. 887-894.
Wu, et.al. "Dibenzothiazoles as Novel Amyloid-Imaging Agents" Bioorganic & Medicinal Chemistry, Elsevier Science Ltd, GB., vol. 15, No. 7, Mar. 12, 2007, pp. 2789-2796.
PCT/EP2008/061275 Int'l Search Report/Written Opinion Dated Jul. 24, 2009.

* cited by examiner

*Primary Examiner* — Michael G Hartley
*Assistant Examiner* — Sean R Donohue

(57) ABSTRACT

The present invention relates to radiopharmaceuticals and in particular to a radiopharmaceutical composition comprising a compound of Formula (I): and polysorbate as an excipient. The radiopharmaceutical composition of the invention reduces problems encountered with prior art compositions comprising the same class of compounds. Also provided by the invention is a method for the preparation of the radiopharmaceutical composition of the invention as well as particular uses of the radiopharmaceutical composition.

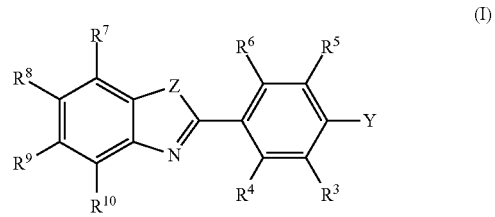

(I)

3 Claims, No Drawings

RADIOPHARMACEUTICAL COMPOSITION

This application is a filing under 35 U.S.C. 371 of international application number PCT/EP2008/061275, filed Aug. 28, 2008, which claims priority of U.S. Provisional application number 60/968,904 filed Aug. 30, 2007, the entire disclosure of which is hereby incorporated by reference.

TECHNICAL FIELD OF THE INVENTION

The present invention relates to a radiopharmaceutical composition comprising an amyloid-binding compound and methods for preparing the same. The radiopharmaceutical composition finds use inter alia in the diagnosis of disease states in which abnormal amyloid deposition is involved. The radiopharmaceutical composition may be useful as an in vivo imaging agent for use in Positron Emission Tomography (PET) or Single Photon Emission Computed Tomography (SPECT).

DESCRIPTION OF RELATED ART

Common excipients included in pharmaceutical compositions include buffers, lyophilisation aids, stabilization aids, solubilisation aids and bacteriostats. The inclusion of one or more optional components in the formulation can improve the stability and shelf-life of the pharmaceutical, as well as the ease of synthesis of the pharmaceutical by the practising end user. Solubilisation aids typically used in the preparation of pharmaceutical compositions include ethanol, glycerin, polyethylene glycol, propylene glycol, polyoxyethylene sorbitan monooleate, sorbitan monooloeate, polysorbates, poly(oxyethylene) poly(oxypropylene)-poly(oxyethylene) block copolymers (Pluronics) and lecithin.

A review by Powell et al provides a comprehensive list of excipients used in pharmaceutical compositions intended for parenteral administration [1998 PDA Journal of Pharmaceutical Science and Technology 52(5) pp 238-311]. There are nearly 40 pharmaceutical compositions listed therein that comprise polysorbate 80, in concentrations ranging from 0.0005 to 12% w/v. A known radiopharmaceutical composition containing a polysorbate is $^{111}$In-oxyquinoline solution. The radiopharmaceutical composition contains, amongst other things, 100 µg of polysorbate 80 per milliliter (equivalent to 0.01% w/v) in order to enable dissolution in water and to prevent binding of the complex when in aqueous solution to glass and plastic surfaces (EP0017355).

In order to be suitable for intravenous administration, radiopharmaceutical compositions must be sterile, non-pyrogenic, and dissolved in a suitable biocompatible carrier medium. To give the desired sterile, pyrogen-free radiopharmaceutical composition, preparation may be under aseptic manufacture conditions. Alternatively, preparation may be under non-sterile conditions, followed by terminal sterilisation using e.g. gamma-irradiation; autoclaving; dry heat; membrane filtration (sometimes called sterile filtration); or chemical treatment (e.g. with ethylene oxide). Sterile filtration can be achieved by means of a dispensing kit through which the radiopharmaceutical composition is passed. Such a dispensing kit must be sterile and typically comprises a 0.2 µm pore filter, along with silicone tubing which permits the radiopharmaceutical composition to pass through the filter and into a suitable sterile receptacle such as a vial or syringe. There is no particular industry standard for such dispensing kits and therefore in practice a variety of filter types and tubing are used in different dispensing kits.

Radiopharmaceuticals are typically prepared by reaction of a non-radioactive precursor compound with a suitable radiolabel, with only a tiny fraction of the precursor compound being radiolabelled to produce the radiopharmaceutical. As a consequence, retention to the surfaces of a dispensing kit can result in the loss of a relatively large proportion of the radiopharmaceutical to the extent that the resulting radiopharmaceutical composition is not fit for use. Radiopharmaceutical compositions comprising thioflavin derivative compounds are known to be useful in the diagnosis of patients having diseases characterised by amyloid deposits, as described in WO2002/16333 and WO2004/083195. The present inventors have found that, when known radiopharmaceutical compositions comprising these thioflavin derivative compounds are passed through dispensing kits, the radiopharmaceutical is strongly retained on a range of different 0.2 µm pore filters and silicone tubings. A solution was therefore sought in order to reduce loss of thioflavin derivative compounds to dispensing kit components.

SUMMARY OF THE INVENTION

The present invention relates to radiopharmaceuticals and in particular to a radiopharmaceutical composition comprising a thioflavin derivative compound with polysorbate as an excipient. The radiopharmaceutical composition of the invention overcomes problems encountered with prior art compositions comprising the same class of compounds. Also provided by the invention is a method for the preparation of the radiopharmaceutical composition of the invention as well as particular uses of the radiopharmaceutical composition.

DETAILED DESCRIPTION OF THE INVENTION

In one aspect, the present invention relates to a radiopharmaceutical composition comprising:
(i) a compound of Formula I:

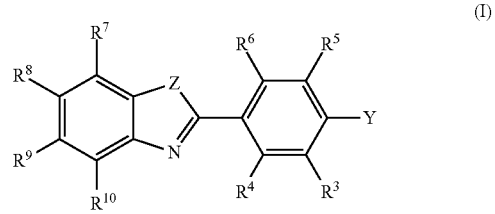

wherein:
Z is S, NR', O, or C(R')$_2$ wherein each R' is independently H or C$_{1-6}$ alkyl, such that the tautomeric form of the heterocyclic ring when Z is C(R')$_2$ is an indole:

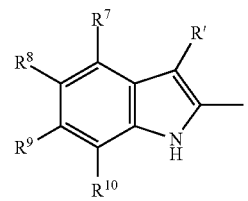

Y is hydrogen, C$_{1-6}$ alkyl, halo, OR' or SR', wherein R' is H or C$_{1-6}$ alkyl, or Y is —NR$^1$R$^2$;
R$^{1-10}$ are each independently selected from the group consisting of hydrogen, C$_{1-6}$ alkyl, C$_{2-6}$ alkenyl, C$_{2-6}$ alkynyl, C$_{1-6}$ alkoxy, $C_{4-6}$ cycloalkyl, hydroxyl, $C_{1-6}$ hydroxyalkyl, $C_{2-6}$ hydroxyalkenyl, $C_{2-6}$ hydroxyalkynyl, thiol, $C_{1-6}$ thioalkyl, $C_{2-6}$ thioalkenyl, $C_{2-6}$ thioalkynyl, $C_{1-6}$ thioalkoxy, halo, $C_{1-6}$ haloalkyl, $C_{2-6}$ haloalkenyl, $C_{2-6}$ haloalkynyl, $C_{1-6}$ haloalkoxy, amino, $C_{1-6}$ aminoalkyl, $C_{2-6}$ aminoalkenyl, $C_{2-6}$ aminoalkynyl, $C_{1-6}$ aminoalkoxy, cyano, $C_{1-6}$ cyanoalkyl, $C_{2-6}$ cyanoalkenyl, $C_{2-6}$ cyanoalkynyl, and $C_{1-6}$ cyanoalkoxy; nitro, $C_{1-6}$ nitroalkyl, $C_{2-6}$ nitroalkenyl, $C_{2-6}$ nitroalkynyl, and $C_{1-6}$ nitroalkoxy; and, wherein at least one atom of said compound of Formula I is a radioactive isotope suitable for in vivo imaging;

(ii) a biocompatible carrier medium; and, (iii) 0.05-5.0% w/v polysorbate;

at a pH of 4.0 to 10.5.

Unless otherwise specified, the term "alkyl" alone or in combination, means a straight-chain or branched-chain alkyl radical containing preferably from 1 to 10 carbon atoms, more preferably from 1 to 5 carbon atoms, most preferably 1 to 3 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl.

The term "alkenyl" denotes an unsaturated straight-chain or branched aliphatic hydrocarbon group containing one double bond. Examples groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" denotes an unsaturated straight-chain or branched aliphatic hydrocarbon group containing one triple bond. Examples include groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Unless otherwise specified, the term "alkoxy", alone or in combination, means an alkyl ether radical wherein the term alkyl is as defined above. Examples of suitable alkyl ether radicals include, but are not limited to, methoxy, ethoxy, n-propoxy, isopropoxy, n-butoxy, iso-butoxy, sec-butoxy, tert-butoxy.

Unless otherwise specified, the term "cycloalkyl", alone or in combination, means a saturated or partially saturated monocyclic, bicyclic or tricyclic alkyl radical wherein each cyclic moiety contains preferably from 3 to 8 carbon atom ring members, more preferably from 3 to 7 carbon atom ring members, most preferably from 4 to 6 carbon atom ring members, and which may optionally be a benzo fused ring system which is optionally substituted as defined herein with respect to the definition of aryl. Examples of such cycloalkyl radicals include, but are not limited to, cyclopropyl, cyclobutyl, cyclopentyl, cyclohexyl, cycloheptyl, octahydronaphthyl, 2,3-dihydro-1H-indenyl, adamantyl.

The term "hydroxyl" refers to a —OH group. The terms "hydroxyalkyl", "hydroxyalkenyl" and "hydroxyalkynyl", as used herein, refer to at least one hydroxy group appended to the parent molecular moiety through an alkyl, alkenyl, alkynyl, or alkoxy, respectively.

The term "halo" means a substituent selected from fluorine, chlorine, bromine or iodine. The terms "haloalkyl", "haloalkenyl", "haloalkynyl", "haloalkoxy" as used herein, refer to at least one halo group appended to the parent molecular moiety through an alkyl, alkenyl, alkynyl, or alkoxy, respectively. Preferred halo substituents are fluoro and iodo.

The term "thiol" means an —SH group. The terms "thioalkyl", "thioalkenyl", "thioalkynyl", "thioalkoxy" as used herein, refer to at least one thiol group appended to the parent molecular moiety through an alkyl, alkenyl, alkynyl, or alkoxy, respectively.

The term "cyano" as used herein refers to a —CN group. The terms "cyanoalkyl", "cyanoalkenyl", "cyanoalkynyl", "cyanoalkoxy" as used herein, refer to at least one cyano group appended to the parent molecular moiety through an alkyl, alkenyl, alkynyl, or alkoxy, respectively. Representative examples of cyanoalkyl include, but are not limited to, cyanomethyl, 2-cyanoethyl, and 3-cyanopropyl.

The term "nitro" means an —NO₂ group. The terms "nitroalkyl", "nitroalkenyl", "nitroalkynyl", "nitroalkoxy" as used herein, refer to at least one nitro group appended to the parent molecular moiety through an alkyl, alkenyl, alkynyl, or alkoxy, respectively.

The term "compound of Formula I" as used herein, means the free compound or alternatively a pharmaceutically acceptable salt, prodrug (such as an ester), or solvate thereof. Suitable salts, prodrugs, and solvates are as described in WO 2004/083195 and WO 02/16333.

Preferably for Formula I:

Z is S, NR' or O; and,

Y is —NR¹R²; and,

R¹⁻¹⁰ are each independently selected from the group consisting of hydrogen, $C_{1-6}$ alkyl, $C_{2-6}$ alkenyl, $C_{2-6}$ alkynyl, $C_{1-6}$ alkoxy, hydroxyl, $C_{1-6}$ hydroxyalkyl, halo, $C_{1-6}$ haloalkyl, and $C_{1-6}$ haloalkoxy.

Most preferably for Formula I:

Z is S;

Y is —NR¹R²; and,

R¹⁻¹⁰ are each independently selected from the group consisting of hydrogen, $C_{1-3}$ alkyl, $C_{2-4}$ alkenyl, $C_{2-4}$ alkynyl, $C_{1-3}$ alkoxy, hydroxyl, $C_{1-3}$ hydroxyalkyl, halo, $C_{1-3}$ haloalkyl, and $C_{1-3}$ haloalkoxy.

In a particularly preferred embodiment, said compound of Formula I is a compound of Formula Ia:

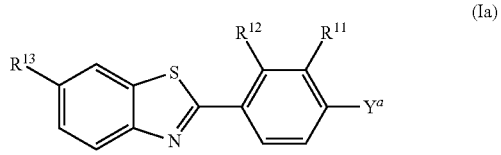

(Ia)

wherein:

R¹¹ and R¹² are independently selected from hydrogen, $C_{1-6}$ alkyl, $C_{1-6}$ alkoxy, nitro, amino, $C_{1-6}$ aminoalkyl, halo or $C_{1-6}$ haloalkyl;

R¹³ is hydrogen, hydroxy, nitro, cyano, $C_{1-6}$ alkyl, $C_{2-6}$ alkenyl, $C_{2-6}$ alkynyl, $C_{1-6}$ alkoxy, halo, $C_{1-6}$ haloalkyl, $C_{1-6}$ haloalkenyl, —COOR', —OCH₂OR', wherein R' is as defined for Formula I; and, $Y^a$ is hydrogen, hydroxyl, $C_{1-6}$ alkyl, $C_{1-6}$ alkoxy or halo, or is —NR¹R² as defined above for Formula I.

Preferably, for the compound of Formula Ia:

R¹¹ and R¹² are independently selected from hydrogen, $C_{1-6}$ alkyl or halo;

R¹³ is hydroxy, $C_{1-6}$ alkyl, $C_{2-6}$ alkenyl, $C_{2-6}$ alkynyl, $C_{1-6}$ alkoxy or halo;

$Y^a$ is halo or —NR¹R² as defined above for Formula I.

Most preferably, for the compound of Formula Ia:

R¹¹ and R¹² are independently selected from hydrogen or halo;

R¹³ is hydroxy or $C_{1-6}$ alkoxy;

$Y^a$ is —$NR^1R^2$ wherein $R^1$ is hydrogen and $R^2$ is hydrogen, $C_{1-6}$ alkyl or $C_{1-6}$ haloalkyl.

A "radioactive isotope suitable for in vivo imaging" is a radioactive isotope which can be detected externally in a non-invasive manner following administration in vivo. Examples of such radioactive isotopes include gamma-emitting radioactive halogens and positron-emitting radioactive non-metals, particularly those suitable for imaging using single-photon emission tomography (SPECT) or positron emission tomography (PET). Suitably, the radioactive isotope is selected from $^{11}$C, $^{123}$I, $^{124}$I, $^{125}$I, $^{131}$I, $^{75}$Br, $^{76}$Br, $^{77}$Br, and $^{18}$F, most suitably $^{11}$C, $^{123}$I, and $^{18}$F In an especially preferred embodiment the radiopharmaceutical composition of the invention is a compound of Formula Ia wherein one of $R^{11}$ to $R^{13}$ or $Y^a$ is, or comprises, radioactive carbon or a radioactive halogen. Preferably, said radioactive carbon is $^{11}$C, and said radioactive halogen is preferably selected from $^{123}$I, $^{124}$I, $^{125}$I, $^{131}$I, $^{75}$Br, $^{76}$Br, $^{77}$Br, $^{17}$F, and $^{18}$F. Most preferably, said radioactive halogen is $^{123}$I or $^{18}$F. Where Formula Ia comprises a radioactive carbon, it is preferably an atom in $Y^a$, most preferably when $Y^a$ is —$NR^1R^2$. Where Formula Ia comprises a radioactive halogen, it is preferably one of $R^{11}$ or $Y^a$, or an atom in $Y^a$ when $Y^a$ is —$NR^1R^2$ with $R^1$ being hydrogen and $R^2$ being $C_{1-6}$ haloalkyl or $C_{2-6}$ haloalkenyl.

Non-limiting examples of the especially preferred compounds of Formula Ia are as follows:

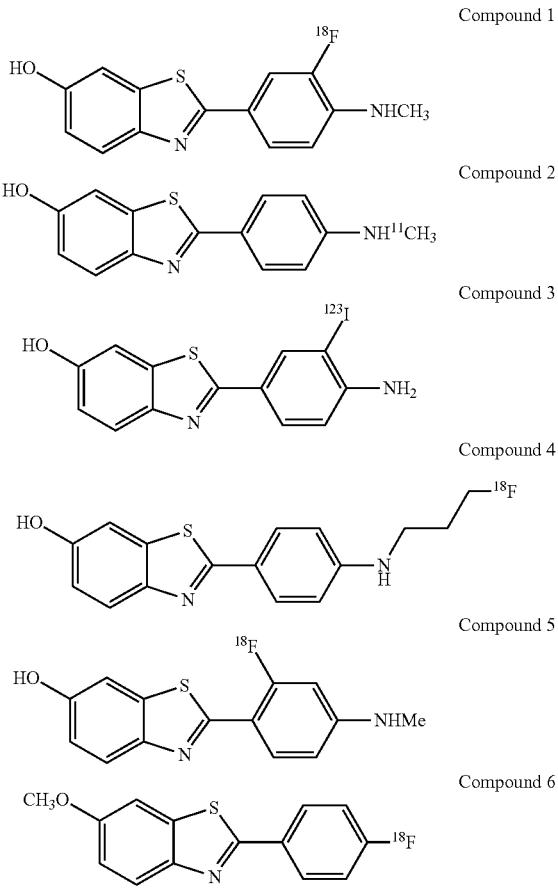

Compound 1

Compound 2

Compound 3

Compound 4

Compound 5

Compound 6

The "biocompatible carrier medium" is a fluid, especially a liquid, in which the radiopharmaceutical is suspended or dissolved, resulting in a radiopharmaceutical composition that is physiologically tolerable, i.e. can be administered to the mammalian body without toxicity or undue discomfort. Typical biocompatible carrier media are, e.g. pyrogen-free water for injection, isotonic saline and aqueous ethanol solution. For the radiopharmaceutical composition of the present invention an aqueous ethanol solution is preferred, with 5-10% (v/v) ethanol being particularly suitable for the composition of the present invention. Preferably, the biocompatible carrier medium is an aqueous ethanol solution comprising 6-8% (v/v) ethanol, most preferably 6.5-7.5% (v/v) ethanol, with 7% (v/v) being especially preferred.

The radiopharmaceutical composition may optionally further comprise additional components such as a pH-adjusting agent, pharmaceutically acceptable stabilisers or antioxidants (such as ascorbic acid, gentisic acid or para-aminobenzoic acid), an antimicrobial preservative or filler.

The term "pH-adjusting agent" means a compound or mixture of compounds useful to ensure that the pH of the radiopharmaceutical composition is maintained within the acceptable limits for mammalian administration (approximately pH 4.0 to 10.5). Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. Preferably, the pH is maintained in the range 6.0 to 8.5, suitably 6.0 to 8.0 and most preferably in the range 5.8 to 7.2, with a pH in the range 7.0 to 7.2 being especially preferred. A preferred buffer for the radiopharmaceutical compositions of the invention is phosphate buffer, preferably 0.005-0.1M, most preferably 0.01M-0.1M, and especially preferably 0.01-0.05M and most especially preferably 0.01-0.02M.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

By the term "filler" is meant a pharmaceutically acceptable bulking agent which may facilitate material handling during product production. Suitable fillers include inorganic salts such as sodium chloride, and water soluble sugars or sugar alcohols such as sucrose, maltose, mannitol or trehalose.

As a general rule for radiopharmaceutical compositions, the aim is to have the lowest quantities of excipients possible that produce a pharmaceutically effective as well as physiologically tolerable composition.

The radiopharmaceutical composition of the invention is suitably supplied for use in a container provided with a seal which is suitable for single or multiple puncturing with a hypodermic needle (e.g. a crimped-on septum seal closure) whilst maintaining sterile integrity. Such containers may contain single or multiple patient doses. Typical dose containers comprise a bulk vial (suitably 5 to 50 cm³, for example 10 to 30 cm³ volume) which contains single or multiple patient doses, whereby a patient dose or doses can thus be withdrawn into clinical grade syringes at various time intervals during the viable lifetime of the preparation to suit the clinical situation. Pre-filled syringes are designed to contain a single patient dose, and are therefore preferably a disposable or other syringe suitable for clinical use. The pre-filled syringe may be provided with a radiopharmaceutical syringe shield to protect the operator from radioactive dose. Suitable such radiopharmaceutical syringe shields are known in the art and preferably comprise either lead or tungsten. Typically, the radiopharmaceutical composition of the invention has a radioactive concentration of 50 to 100 MBq/ml, suitably 70 to 85 MBq/ml, more suitably 80 MBq/ml. A single patient dose will typically contain 50 to 400 MBq, more typically 80 to 370 MBq at the time of administration and will have a volume of 1 to 10 ml, preferably around 5 ml.

A "polysorbate" is a polyoxyethylene sorbitan ester. A comprehensive description of polysorbates can be found in "Nonionic Surfactants", M. J. Schick, Ed. (Dekker, New York, 1967) pp 247-299. Examples of polysorbates include polysorbate 20, polysorbate 40, polysorbate 60 and polysorbate 80, which are commercially available under the trade name Tween® as Tween 20, Tween 40, Tween 60 and Tween 80, respectively, from Sigma-Aldrich. The number following "polysorbate" is related to the type of fatty acid associated with the polyoxyethylene sorbitan part of the molecule. Monolaurate is indicated by 20, monopalmitate is indicated by 40, monostearate by 60 and monooleate by 80. The concentration of polysorbate is suitably sufficient to eliminate substantially all binding of the compound of Formula I to a range of filter types. Preferably, the loss of compound of Formula I to the filter during dispensing is in the range 0-10%, most preferably 0-5.0%, especially preferably 0-1.0%, and most especially preferably 0%. In a preferred embodiment, the polysorbate of said radiopharmaceutical formulation is selected from polysorbate 20 or polysorbate 80, with polysorbate 80 being particularly preferred. Preferably, the concentration of polysorbate present in the radiopharmaceutical formulation is in the range 0.25-2.5% w/v, most preferably between 0.5 and 1.0% w/v, and especially preferably 0.5% w/v.

Compounds of Formula I may be prepared from commercially available starting materials or using starting materials as described in WO2002/16333, WO2004/083195 and WO2007/020400, or by standard methods of organic chemistry.

Compounds of Formula I comprising a radiolabel such as radioactive carbon or a radioactive halogen may be conveniently prepared by reaction of a precursor compound with a suitable source of the radioactive carbon or radioactive halogen.

A "precursor compound" comprises a derivative of a radiolabelled compound of Formula I, designed so that chemical reaction with a convenient chemical form of the radiolabel occurs site-specifically; can be conducted in the minimum number of steps (ideally a single step); and without the need for significant purification (ideally no further purification), to give the desired radiolabelled compound of Formula I. Such precursor compounds are synthetic and can conveniently be obtained in good chemical purity. The precursor compound may optionally comprise a protecting group for certain functional groups of the precursor compound.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired radiolabelled compound of Formula I is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

Compounds of Formula I that are labelled with a radioactive halogen or radioactive carbon are preferred in the radiopharmaceutical composition of the invention. Methods for obtaining radioiodinated, radiofluorinated and radiocarbonylated compounds of Formula I via suitable precursor compounds are now described.

Radioiodination

Where the compound of Formula I is labelled with radioiodine, suitable precursor compounds are those which comprise a derivative which either undergoes electrophilic or nucleophilic iodination or undergoes condensation with a labelled aldehyde or ketone. Examples of the first category are:

(a) organometallic derivatives such as a trialkylstannane (eg. trimethylstannyl or tributylstannyl), or a trialkylsilane (eg. trimethylsilyl) or an organoboron compound (eg. boronate esters or organotrifluoroborates);

(b) a non-radioactive alkyl bromide for halogen exchange or alkyl tosylate, mesylate or triflate for nucleophilic iodination;

(c) aromatic rings activated towards electrophilic iodination (e.g. phenols, phenylamines) and aromatic rings activated towards nucleophilic iodination (e.g. aryl iodonium salt aryl diazonium, aryl trialkylammonium salts or nitroaryl derivatives).

The precursor compound for radioiodination preferably comprises: a non-radioactive halogen atom such as an aryl iodide or bromide (to permit radioiodine exchange); an activated aryl ring (e.g. a phenol or phenylamine); an organometallic substituent (e.g. trialkyltin, trialkylsilyl or organoboron compound); or an organic substituent such as triazenes or a good leaving group for nucleophilic substitution such as an iodonium salt. Preferably for radioiodination, the precursor compound comprises an activated aryl ring or an organometallic substituent, said organometallic substituent most preferably being trialkyltin.

Precursor compounds and methods of introducing radioiodine into organic molecules are described by Bolton [J. Lab. Comp. Radiopharm., 45, 485-528 (2002)]. Suitable boronate ester organoboron compounds and their preparation are described by Kabalaka et al [Nucl. Med. Biol., 29, 841-843 (2002) and 30, 369-373(2003)]. Suitable organotrifluoroborates and their preparation are described by Kabalaka et al [Nucl. Med. Biol., 31, 935-938 (2004)].

Examples of aryl groups to which radioactive iodine can be attached are given below:

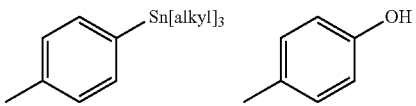

wherein alkyl in this case is preferably methyl or butyl. These groups contain substituents which permit facile radioiodine substitution onto the aromatic ring. Alternative substituents containing radioactive iodine can be synthesised by direct iodination via radiohalogen exchange, e.g.

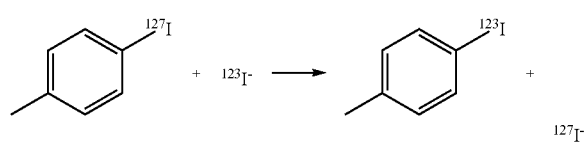

The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine.

The source of the radioiodine is chosen from iodide ion or the iodonium ion ($I^+$). Most preferably, the chemical form is iodide ion, which is typically converted to an electrophilic species by an oxidant during radiosynthesis.

More detail relating to certain methods of radioiodination of compounds of Formula I is provided in WO2002/16333 and WO2004/083195.

Radiofluorination

When the compound of Formula I is labelled with a radioactive isotope of fluorine the radiofluorine atom may form part of a fluoroalkyl or fluoroalkoxy group, since alkyl fluorides are resistant to in vivo metabolism. Fluoroalkylation may be carried out by reaction of a precursor compound containing a reactive group such as phenol, thiol and amide with a fluoroalkyl group.

Alternatively, the radiofluorine atom may be attached via a direct covalent bond to an aromatic ring such as a benzene ring. For such aryl systems, $^{18}F$-fluoride nucleophilic displacement from an aryl diazonium salt, aryl nitro compound or an aryl quaternary ammonium salt are suitable routes to aryl-$^{18}F$ derivatives.

Radiofluorination may be carried out via direct labelling using the reaction of $^{18}F$-fluoride with a suitable chemical group in the precursor compound having a good leaving group, such as an alkyl bromide, alkyl mesylate or alkyl tosylate.

As the half-life of $^{18}F$ is only 109.8 minutes, it is important that the intermediate $^{18}F$ moieties have high specific activity and, consequently, are produced using a reaction process which is as rapid as possible.

More detail relating to certain methods of radiofluorination of compounds of Formula I is provided in WO2002/16333, WO2004/083195 and WO2007/020400.

Further details of synthetic routes to $^{18}F$-labelled derivatives are described by Bolton, J. Lab. Comp. Radiopharm., 45, 485-528 (2002).

Radiocarbonylation

Where the compound of Formula I is labelled with $^{11}C$, one approach to labelling is to react a precursor compound which is the desmethylated version of a methylated compound of Formula I with [$^{11}C$]methyl iodide. It is also possible to incorporate $^{11}C$ by reacting Grignard reagent of the particular hydrocarbon chain of the desired labelled compound of Formula I with [$^{11}C$]$CO_2$. $^{11}C$ could also be introduced as a methyl group on an aromatic ring, in which case the precursor compound would include a trialkyltin group or a $B(OH)_2$ group.

As the half-life of $^{11}C$ is only 20.4 minutes, it is important that the intermediate $^{11}C$ moieties have high specific activity and, consequently, are produced using a reaction process which is as rapid as possible.

More detail relating to certain methods of radiocarbonylation of compounds of Formula I is provided in WO2002/16333 and WO2004/083195.

A thorough review of such $^{11}C$-labelling techniques may be found in Antoni et al "Aspects on the Synthesis of $^{11}C$-Labelled Compounds" in Handbook of Radiopharmaceuticals, Ed. M. J. Welch and C. S. Redvanly (2003, John Wiley and Sons).

When a compound of Formula I is radiolabelled, the precursor compound may be conveniently provided as part of a kit, for example for use in a radiopharmacy. Such a kit may contain a cartridge which can be plugged into a suitably adapted automated synthesiser. The cartridge may contain, apart from the precursor, a column to remove any unwanted radioactive ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers' requirements for radioactive concentration, volumes, time of delivery, etc. Conveniently, all components of the kits are disposable to minimise the possibility of contamination between runs and may be sterile and quality assured.

Following synthesis, the compound of Formula I may require purification which may be effected using standard methods, for example using high-performance liquid chromatography (HPLC), ion-exchange chromatography, and/or passing through a solvent exchange cartridge.

High performance liquid chromatography (HPLC) is a commonly-used method in the preparation of radiopharmaceuticals and may be used to remove any chemical impurities present in the crude reaction mixture following synthesis of the compound of Formula I. For any particular compound, the HPLC method needs to be optimised. A normal phase or reverse phase column can be used with one of a variety of organic solvents, e.g. methanol, acetonitrile, ethanol, 2-propanol at neutral, acidic or basic pH. Preferably a reverse phase column is used with neutral pH conditions to achieve the most favourable separation of a compound of Formula I.

Purification using a solvent exchange cartridge involves loading of the compound of Formula I onto the column followed by elution of the column with a suitable solvent, for the compounds of Formula I, ethanol and aqueous ethanol are preferred solvents. Suitable solvent exchange cartridges include SEP-Pak™ cartridges (Waters), such as C8, C18 or C30.

In a further aspect, the present invention relates to a method for preparation of the radiopharmaceutical composition of the invention comprising the following steps:
  (i) admixing a compound of Formula I, a biocompatible carrier medium, and 0.05-5.0% w/v polysorbate;
  (ii) if necessary, adjusting the pH of the resultant mixture to be 4.0 to 10.5.

Following step (ii), the composition may be sterilised. Sterilisation may be effected by standard methods of the art, for example gamma-irradiation; autoclaving; dry heat; membrane filtration (sometimes called sterile filtration); or chemical treatment (e.g. with ethylene oxide). Sterile filtration can be achieved by means of a dispensing kit through which the radiopharmaceutical composition is passed. Such a dispensing kit must be sterile and typically comprises a 0.2 µm pore filter, along with silicone tubing which permits the radiopharmaceutical composition to pass through the filter and into a suitable sterile receptacle such as a vial or syringe.

Accordingly, there is further provided a method for preparation of the radiopharmaceutical composition of the invention as described above which further comprises the step:
(iii) sterilisation of the composition resulting from step (ii), preferably by sterile filtration.

Step (i) may conveniently be effected by loading the compound of Formula I onto a solvent exchange cartridge as described above, and then eluting with a solvent or mixture of solvents comprised in the biocompatible carrier medium (for example, water and ethanol). The eluate may be collected in a collection container such as a vial, pre-filled with the polysorbate and any other excipients such as a filler (for example, sodium chloride) and pH-adjusting agent (for example a pharmaceutically acceptable buffer, such as phosphate buffer). In one preferred embodiment, the collection container is pre-filled as described and then stored at reduced temperature of −30° C. to −10° C., suitably −25° C. to −15° C., more suitably at −20° C. and then brought to ambient temperature shortly before use. It has been found that storage of the polysorbate in this way increases its shelf-life and enables production of a radiopharmaceutical composition having higher radioactive concentration (RAC).

In step (i), the compound of Formula I, the biocompatible carrier medium and the polysorbate and preferred embodiments therefor are each as defined above. As described above, a preferred biocompatible carrier medium is aqueous ethanol.

Step (ii) of the method of preparation may be performed during step (i) or thereafter. For example, as described above, a pH adjusting agent may be in the pre-filled collection container during step (i) or may be added thereto during or after performance of step (i).

In a preferred embodiment of the method of preparation, one or more steps is automated, as described above.

Examples 1 to 4 demonstrate the advantages of the compositions and methods of the invention in reducing the retention of Compound 1 to a range of dispensing kit components during sterile filtration.

In a yet further aspect, the present invention relates to the radiopharmaceutical composition of the invention for use in the determination of the presence, location and/or amount of one or more amyloid deposits in an organ or body area of a subject. Preferably, the amyloid deposits are deposits of amyloid β, and the organ or body area of the subject is the brain. The radiopharmaceutical composition of the invention is for in vivo imaging of one or more amyloid deposits in a subject suspected of having an amyloid condition. An "amyloid condition" is a disorder or condition characterised by amyloid deposition, such as Alzheimer's disease (AD), familial AD, Down's syndrome, amyloidosis, type II diabetes mellitus, and homozygotes for the apolipoprotein E4 allele. The method of the invention is preferably for in vivo imaging of AD. The term "in vivo imaging" refers to any method which permits the detection of a compound of Formula I following administration of the radiopharmaceutical composition of the invention to a subject. Preferred methods of in vivo imaging are positron emission tomography (PET) and single-photon emission tomography (SPECT), with PET being especially preferred. A "subject" is a mammal, preferably a human. In an alternative embodiment, the method of the invention may be carried out at two or more distinct points in time as a means to monitor the progression or remission of an amyloid condition, typically in response to an amyloid condition-specific treatment.

Accordingly, there is provided a method for determination of the presence, location, and/or amount of one or more amyloid deposits in an organ or body area of a subject which comprises the steps:
(I) administration to a subject of a detectable quantity of the radiopharmaceutical composition of the invention;
(ii) allowing the compound of Formula I to bind to any amyloid deposits in said subject; and,
(iii) determination by in vivo imaging of the presence, location and/or amount of one or more amyloid deposits in said subject.

Steps (ii) and (iii) above can also be understood to be a standalone use of the radiopharmaceutical composition of the invention for the determination of the presence, location and/or amount of one or more amyloid deposits in a subject pre-administered with said radiopharmaceutical composition.

A "detectable quantity" means that the amount of the radiopharmaceutical composition administered is sufficient to enable detection of binding of the compound of Formula I to amyloid in a subject. Injected activities are typically 50 to 400 MBq, more typically 80 to 370 MBq and will have a volume of 1 to 10 ml, preferably around 5 ml.

This aspect of the invention also encompasses use of a compound of Formula I in the manufacture of the radiopharmaceutical composition of the invention for use in determining the presence, location and/or amount of one or more amyloid deposits in an organ or body area of a subject.

BRIEF DESCRIPTION OF THE EXAMPLES

Example 1 describes experiments carried out to compare formulations of [$^{19}$F]Compound 1 having PEG 400, propylene glycol or polysorbate 20.

Example 2 describes experiments carried out to compare formulations of [$^{19}$F]Compound 1 having polysorbate 20 or polysorbate 80.

Example 3 describes experiments carried out to compare sticking of formulations of [$^{19}$F]Compound 1 having polysorbate 80 onto two different filter types.

Example 4 describes experiments carried out to compare sticking of formulations of [$^{19}$F]Compound 1 having polysorbate 80 onto three different silicone tubing types.

Example 5 describes automated synthesis of [$^{18}$F]Compound 1 and its formulation into a composition of the invention.

EXAMPLES

Example 1

Sterile Dispensing of Compound 1 Formulations with PEG 400 and Propylene Glycol

Solutions were prepared containing 7% v/v ethanol in 0.01 M sodium phosphate buffer at pH 7.4, 75 µg of Compound 1 and either (i) 12% v/v propylene glycol (PG) or (ii) 10% v/v polyethylene glycol 400 (PEG 400). Percentage loss of Compound 1 to various components of a dispensing kit was evaluated by High Performance Liquid Chromatography (HPLC) in the following experiments:

| Sample | Sample Composition | | Treatment | Treatment time | Volume treated (ml) | % loss |
| --- | --- | --- | --- | --- | --- | --- |
| | PG (% v/v) | PEG 400 (% v/v) | | | | |
| 1 | 12 | 0 | Syringe | 1 min 4 sec | 9.5 | 0 |
| 2 | 12 | 0 | Silicone tube | 2 min 23 sec | ~1-1.5 | 30 |
| 3 | 12 | 0 | Hard tube | 5 min 2 sec | ~2-2.5 | 3 |
| 4 | 12 | 0 | Filter | 10 sec | 9.5 | 87 |
| 5 | 0 | 10 | Syringe | 1 min 1 sec | 9.5 | 1 |

-continued

| Sample | Sample Composition PG (% v/v) | PEG 400 (% v/v) | Treatment | Treatment time | Volume treated (ml) | % loss |
|---|---|---|---|---|---|---|
| 6 | 0 | 10 | Silicone tube | 2 min 2 sec | ~1-1.5 | 8 |
| 7 | 0 | 10 | Hard tube | 5 min 4 sec | ~2-2.5 | 4 |
| 8 | 0 | 10 | Filter | 11 sec | 9.5 | 51 |

For both excipients the amount lost in the syringe and hard tube was small. Major loss was seen in the filter and for propylene glycol also in the silicone tube. These results demonstrate that even in the presence of 12% PG or 10% PEG 400, significant loss of Compound 1 to the surfaces of the dispensing kit was observed, most markedly to the filter.

Example 2

Comparison of Sterile Filtration of Compound 1 Compositions with Polysorbate 20 and Polysorbate 80

Solutions were prepared containing 7% v/v ethanol in 0.01M sodium phosphate buffer at pH 7.4, 75 µg of Compound 1 and selected v/v % amounts of polysorbate 20 and polysorbate 80. 4 filtration experiments were carried out as follows:

| Experiment | Polysorbate 20 v/v % | Polysorbate 80 v/v % |
|---|---|---|
| 1 | 0.1 | 0 |
| 2 | 5.0 | 0 |
| 3 | 0 | 0.1 |
| 4 | 0 | 5.0 |

Each solution was withdrawn into a 10 ml syringe, the volume turning out to be approximately 9.5 ml. The volume in the syringe was justified down to 9 ml; the remnant was used as sample for analysis before filtration (untreated reference).

Filtration was carried out through a Pall S-200 DLL 25 Repel™ Stripe filter, with 25 mm diameter, "Supor® hydrophilic polyethersulfone and hydrophobic band Repel membrane", 0.20 µm pore and 2.80 cm" (Pall filter). 1 ml of solution was pressed through the filter per fraction. Of the first fraction of 1 ml only approx. 0.4 ml came through (dead volume approx. 0.6 ml). The remaining fractions were 1 ml apart from the last fraction which was approx. 1.9 ml, while air was also pressed through to collect the whole volume of the solution. The volume of the fractions was measured by use of an automatpipette.

The Tween-solutions were foaming slightly, so the solutions had to be pressed carefully through the filter (average time for filtering 9 ml was approx. 1 min and 20 sec).

Recovery after filtration was as follows:

| Fraction | Polysorbate 20 0.1% | Polysorbate 20 5.0% | Polysorbate 80 0.1% | Polysorbate 80 5.0% |
|---|---|---|---|---|
| 1 | 6 | 99 | 0 | 98 |
| 2 | 86 | 89 | 59 | 102 |
| 3 | 88 | 105 | 97 | 101 |
| 4 | 98 | 103 | 101 | 101 |
| 5 | 99 | 104 | 102 | 102 |
| 6 | 100 | 104 | 99 | 101 |
| 7 | 97 | 104 | 101 | 103 |
| 8 | 97 | 103 | 105 | 102 |
| 9 | 102 | 105 | 105 | 101 |

The total recovery after filtration was 92% for 0.1% polysorbate 20 and 80, and 100% for 5.0% polysorbate 20 and 80. These results demonstrate that even at low concentrations, the presence of either polysorbate 20 or polysorbate 80 in a formulation of Compound I resulted in a significant reduction in the loss of Compound I to the filter.

Example 3

Comparison of Sterile Filtration of Compound 1 Compositions on Various Filter Types Solutions were prepared containing 7% v/v ethanol in 10 mM sodium phosphate buffer at pH 7.4, 75 µg of Compound 1 and selected v/v % amounts of polysorbate 80. 10 filtration experiments were carried out using the Pall filter as well as a Millipore Millex® GV 33 mm filter unit 0.22 µm with Durapore® membrane (Millex filter), and various v/v % amounts of polysorbate 80, as follows:

| Experiment | Filter | Polysorbate 80 (v/v %) |
|---|---|---|
| 1 | Pall | 0.03 |
| 2 | Pall | 0.1 |
| 3 | Pall | 0.3 |
| 4 | Pall | 1.0 |
| 5 | Pall | 5.0 |
| 6 | Millex | 0.03 |
| 7 | Millex | 0.1 |
| 8 | Millex | 0.3 |
| 9 | Millex | 1.0 |
| 10 | Millex | 5.0 |

Each solution was withdrawn into a 10 ml syringe, the volume turning out to be approximately 9.5 ml. The volume in the syringe was justified down to 9 ml; the remnant was used as sample for analysis before filtration (untreated reference).

Each solution was pressed through the filter indicated above in one go, taking approximately 16 seconds. The % recovery after filtration calculated based on area of Compound 1 was as follows:

| Polysorbate 80 v/v % | Pall | Millex |
|---|---|---|
| 0.03 | 72 | 101 |
| 0.1 | 92 | 100 |
| 0.3 | 95 | 101 |
| 1.0 | 95 | 104 |
| 5.0 | 100 | 101 |

These results clearly demonstrate that the presence of polysorbate 80 at concentrations of at least 0.3% v/v is sufficient to reduce loss of Compound 1 even to filters where pronounced loss had previously been observed.

Example 4

Comparison of Compound 1 Adsorption to Various Silicone Tubings

Solutions were prepared containing 7% v/v ethanol in 10 mM sodium phosphate buffer at pH 7.4, 75 μg of Compound 1 and selected v/v % amounts of polysorbate 80. Various silicone tubing types were tested as follows:

| Experiment | Silicone Tubing | Polysorbate 80 v/v % |
|---|---|---|
| 1 | 0.8 × 4.0 Pt-cured* | 0 |
| 2 | 1.6 × 4.8 Pt-cured** | 0 |
| 3 | 1.6 × 4.8 Perox-cured*** | 0 |
| 4 | 0.8 × 4.0 Pt-cured* | 1 |
| 5 | 1.6 × 4.8 Pt-cured** | 1 |
| 6 | 1.6 × 4.8 Perox-cured*** | 1 |
| 7 | 0.8 × 4.0 Pt-cured* | 5 |
| 8 | 1.6 × 4.8 Pt-cured** | 5 |
| 9 | 1.6 × 4.8 Perox-cured*** | 5 |

*AdvantaPure ® silikonslange Platinum-cured 0.8 mm inner diameter
**AdvantaPure silikonslange Platinum-cured 1.6 mm inner diameter
***Mediline (Angleur, Belgium) silicone tubing peroxide-cured 1.6 mm inner diameter The percentage loss of Compound 1 onto the tubing was calculated in each experiment. Fluorine was assayed before and after the passage through tubing, and the results were as follows:

| Experiment | Treatment Time | Volume Treated (μl) | % Loss Compound 1 |
|---|---|---|---|
| 1 | 2 min 0 sec | 350 | 63 |
| 2 | 2 min 7 sec | 1400 | 41 |
| 3 | 2 min 6 sec | 1400 | 45 |
| 4 | 2 min 3 sec | 350 | 0 |
| 5 | 2 min 10 sec | 1400 | 1 |
| 6 | 2 min 4 sec | 1400 | 0 |
| 7 | 2 min 2 sec | 350 | 0 |
| 8 | 2 min 4 sec | 1400 | 1 |
| 9 | 2 min 1 sec | 1400 | 1 |

These results demonstrate that the significant loss of Compound 1 to each tubing type was reduced or even eliminated with the inclusion of at least 1.0% v/v polysorbate in the formulation.

Example 5

Automated Synthesis of 2-[3-[$^{18}$F]fluoro-4-(methylamino)phenyl]-6-hydroxy-benzothiazole (Compound 1)

A single-use fluid pathway for a FASTlab™ (GE Healthcare) automated synthesiser unit was loaded with following reagents and mounted onto the FASTlab platform:
I. 150 mM tetrabutylammonium bicarbonate in 80:20 acetonitrile:water (0.8 ml)
II. Final intermediate solution: 75 mM 2-[3-nitro-4(methylformylamino)phenyl]-6-ethoxymethoxy-benzothiazole in dimethylsulfoxide (1.37 ml)
III. 4 M hydrochloric acid (4 ml)
IV. Ethanol (2×4 ml)
V. Water (100 ml)

In addition, a product collection vial containing the following excipients was located adjacent to the FASTlab platform: 0.67% (w/v) polysorbate 80, 1.21% (w/v) sodium chloride, 18.82 mM phosphate buffer, pH 7; (total volume 37.2 ml).

When a solution of [$^{18}$F]fluoride in [$^{18}$O]-enriched water had been loaded into the synthesiser's starting position, the operator initiated the programme causing the following sequence of events to take place:

The fluoride solution passed through a QMA (quaternary methyl ammonium) cartridge, trapping the fluoride and sending the enriched water to waste. The QMA cartridge was then eluted with 350 μl of the 150 mM tetrabutylammonium bicarbonate solution in order to recover the fluoride and the resultant solution was passed into the reactor vessel.

What is claimed is:
1. A radiopharmaceutical composition comprising:

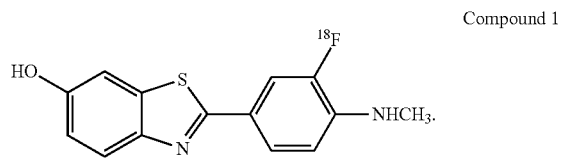 [SMILES: CNc1ccc(-c2nc3ccc(O)cc3s2)cc1[18F]]

Compound 1

(ii) a biocompatible carrier medium of aqueous ethanol; and,
(iii) 0.25-2.5% w/v polysorbate;
at a pH of 4.0 to 10.5.
2. The radiopharmaceutical composition of claim 1 wherein said polysorbate is 0.5-1.0% w/v polysorbate.
3. The radiopharmaceutical composition of claim 1 wherein said polysorbate is polysorbate 80.

* * * * *